(12) United States Patent
Müller-Hasky et al.

(10) Patent No.: US 8,058,428 B2
(45) Date of Patent: Nov. 15, 2011

(54) METHOD FOR PRODUCING MELAMINE

(75) Inventors: Martin Müller-Hasky, Heusenstamm (DE); Jürgen Eberhardt, Rodgau (DE); Arne Schadt, Bad Nauheim (DE)

(73) Assignee: Lurgi AG, Frankfurt am Main (DE)

( * ) Notice: Subject to any disclaimer, the term of this patent is extended or adjusted under 35 U.S.C. 154(b) by 648 days.

(21) Appl. No.: 11/919,603

(22) PCT Filed: Feb. 27, 2006

(86) PCT No.: PCT/EP2006/001769
§ 371 (c)(1),
(2), (4) Date: Oct. 30, 2007

(87) PCT Pub. No.: WO2006/119814
PCT Pub. Date: Nov. 16, 2006

(65) Prior Publication Data
US 2009/0076265 A1    Mar. 19, 2009

(30) Foreign Application Priority Data

May 6, 2005   (DE) ............................ 102005021084
May 13, 2005  (DE) ............................ 102005023042

(51) Int. Cl.
  *C07D 251/60*   (2006.01)
  *C07D 251/62*   (2006.01)
(52) U.S. Cl. ........................ 544/203; 544/201
(58) Field of Classification Search ............ 544/203, 544/201, 201.203
See application file for complete search history.

(56) References Cited

U.S. PATENT DOCUMENTS

| | | | |
|---|---|---|---|
| 3,290,309 A | 12/1966 | Marten | 260/249.7 |
| 3,321,603 A | 5/1967 | Hamprecht | |
| 3,386,999 A | 6/1968 | Manes | 260/249.7 |
| 3,503,970 A | 3/1970 | Kazumichi | 260/249.7 |
| 3,547,919 A | 12/1970 | Hamprecht | 260/249.7 |
| 3,555,784 A | 1/1971 | Mohr | 55/70 |
| 3,578,413 A | 5/1971 | Vorage | 23/260 |
| 3,697,519 A | 10/1972 | Kaasenbrood | 260/249.7 |
| 4,348,520 A | 9/1982 | Bruls et al. | 544/201 |
| 6,355,797 B2 * | 3/2002 | Coufal | 544/201 |
| 6,730,142 B2 | 5/2004 | Reyes | |
| 2001/0005751 A1 | 6/2001 | Coufal | 544/200 |
| 2003/0177903 A1 | 9/2003 | Reyes et al. | 95/143 |
| 2006/0100428 A1 * | 5/2006 | Tjioe et al. | 544/203 |

FOREIGN PATENT DOCUMENTS
GB    937 561    9/1963
GB    937561     9/1963

OTHER PUBLICATIONS

Crews et al: "Melanime and Guanamines", Ulmann's Encyclopedia of Industrial Chemistry, vol. 21, 2003, pp. 205-216, XP002393510, pp. 208-211.

* cited by examiner

*Primary Examiner* — Venkataraman Balasubramanian
(74) *Attorney, Agent, or Firm* — Jonathan Myers; Andrew Wilford

(57) ABSTRACT

The invention concerns a method for producing melamine by dissolving urea, in which solid, liquid or gaseous media other than the gas mixture consisting of the components formed during the reaction is used to desublime the melamine from the gas phase.

2 Claims, 3 Drawing Sheets

METHOD FOR PRODUCING MELAMINE

CROSS REFERENCE TO RELATED APPLICATIONS

This application is the US national phase of PCT application PCT/EP2006/001769, filed 27 Feb. 2006, published 27 Feb. 2006 as WO 2006/119814, and claiming the priority of German patent application 1020050201984 itself filed 6 May 2005 and German patent application 102005023042.3 itself filed 13 May 2005, whose entire disclosures are herewith incorporated by reference.

FIELD OF THE INVENTION

The invention relates to a method of producing melamine by the decomposition of urea with subsequent desublimation of melamine from the gaseous phase in a crystallization apparatus.

BACKGROUND OF THE INVENTION

The production of melamine starting from urea is a method that has been known for quite some time, a distinction being drawn between two types of processes: The noncatalytic high-pressure process and the catalytic low-pressure process. The high-pressure process requires pressures of at least 8 MPa, while the catalytic low-pressure process is carried out in a fluidized bed at a pressure of 0.1 to a maximum of 1 MPa with temperatures of at least 380 to 410° C. The carrier gas used for the low-pressure method is either ammonia or a mixture of carbon dioxide and ammonia, the resulting melamine being present in gaseous form after the reaction.

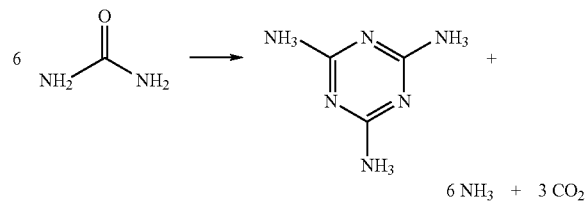

The yield of melamine with this method relative to the quantity of urea used is 90 to 95%. In the literature, the three most frequently used low-pressure methods are known as BASF, Chemie Linz and Stamicarbon processes.

The BASF process is a single-stage reaction method (FIG. 1), where molten urea is reacted in a fluidized bed at a temperature of 395 to 400° C. under nearly atmospheric pressure. In addition to melamine and urea, the resulting reaction gas contains traces of by-products such as melem and melam as well as a reaction gas comprising ammonia and carbon dioxide. The reaction gas mixture that is obtained is then cooled, the removed catalyst and the crystallized by-products are separated and the reaction gas comprising the melamine is fed to a crystallizer. In the crystallizer, the hot gas comprising the melamine is cooled with cold reaction gas (quenching gas), which lowers the temperature of the melamine-containing gas to 190 to 220° C. Under these conditions, melamine desublimes approximately 98% from the reaction gas. After separating the melamine, the remaining gas (recycle gas) is pumped to a urea washing station by means of a recycle gas blower, is cooled and washed in direct contact with the molten urea and then recirculated into the reactor. The temperature of the quenching gas is ~138° C., so that it is necessary to admix 2.5 to 3.5 kg of quenching gas per kilogram of melamine-containing gas to adjust a temperature of 190 to 220° C. in the crystallization apparatus.

The separation of melamine from melamine-containing gas mixtures is a process that has been well-known for quite some time.

German unexamined patent application 1,204,679 [U.S. Pat. No. 3,321,603], for example, describes the separation of melamine from a gas stream by cooling on cold walls, or by contacting it with a cold inert gas stream, a cold inert fluid or cold inert solid mass.

The commonly used method of separating melamine by contacting it with a cold inert gas stream, however, has the disadvantage that very large quenching gas volumes relative to the reaction gas volume are required for the necessary temperature reduction. The ratio is approximately 4 to 1. Due to the large volume of gas, apparatuses with accordingly large dimensions are required, which is associated with corresponding added financial expenses in the production of melamine and with higher investment expenditures. In addition, the gases leaving the product cyclone must be cleaned and recirculated with the help of the recycle gas blower. Also, the recycle gas is still saturated with melamine and desublimes melamine every time the temperature is lowered further. This type of melamine adhesion also occurs at undesirable sites such as the recycle gas blower, resulting in drastically shortened plant operating life, undesirable production failure and an increased need for maintenance.

OBJECT OF THE INVENTION

It is therefore the object of the invention to provide a method that allows the separation of melamine from melamine-containing reaction gases in a cost-efficient manner, without the use of quenching gas and without the use of a compressor n (FIG. 1).

SUMMARY OF THE INVENTION

This object is achieved by the inventive method of producing melamine in that other solid, liquid or gaseous components than the gas mixture comprising the components formed during the reaction (quenching gas) are used for the desublimation of the gaseous melamine.

The advantages achieved with this invention are that as a result of the use of other solid, liquid or gaseous components than the conventional quenching gas for the desublimation of gaseous melamine the gas volume circulating in the process is clearly reduced, resulting in smaller apparatuses and pipe dimensions, which in turn lower the investment costs.

Furthermore, the compressor required with the use of quenching gas can be eliminated. By eliminating the quenching gas line p (FIG. 1), the reduced recycle gas volume can be pumped directly by the existing compressor n (FIG. 1).

Advantageously it is possible to desublime melamine-containing reaction gas by feeding crystalline melamine at the same time.

It is also possible to cool the melamine-containing reaction gas in the reaction vessel from approximately 350° C. to approximately 190° C. by introducing crystalline melamine. According to a preferred feature, it is also possible that the crystalline melamine used for quenching has a temperature of less than 100° C. A temperature of approximately 40° C. is preferred. It is preferable if the temperature of the melamine removed from the crystallization vessel is regulated by the amount of crystalline melamine to be used for quenching, where this temperature should not be below 190° C. It is particularly advantageous if the majority of melamine removed from the crystallization vessel is reintroduced in the loop into the crystallization vessel and used to quench the hot melamine-containing reaction gases. A further development enables the desublimation of melamine with liquid or gaseous ammonia. In an advantageous embodiment, the melamine-containing reaction gases are cooled from 350° C. to 190° C. by introducing liquid ammonia. It is beneficial if the ammonia used has a pressure of 0.01 to 0.26 MPa and a temperature of −34 to +60° C. The temperature of the removed melamine can thus be regulated by the amount of ammonia that is used, the temperature being preferably 190° C.

BRIEF DESCRIPTION OF THE DRAWINGS

Embodiments of the invention are illustrated in the drawings and described in detail hereinafter. Therein.

DETAILED DESCRIPTION OF THE DRAWING

Figure 1:
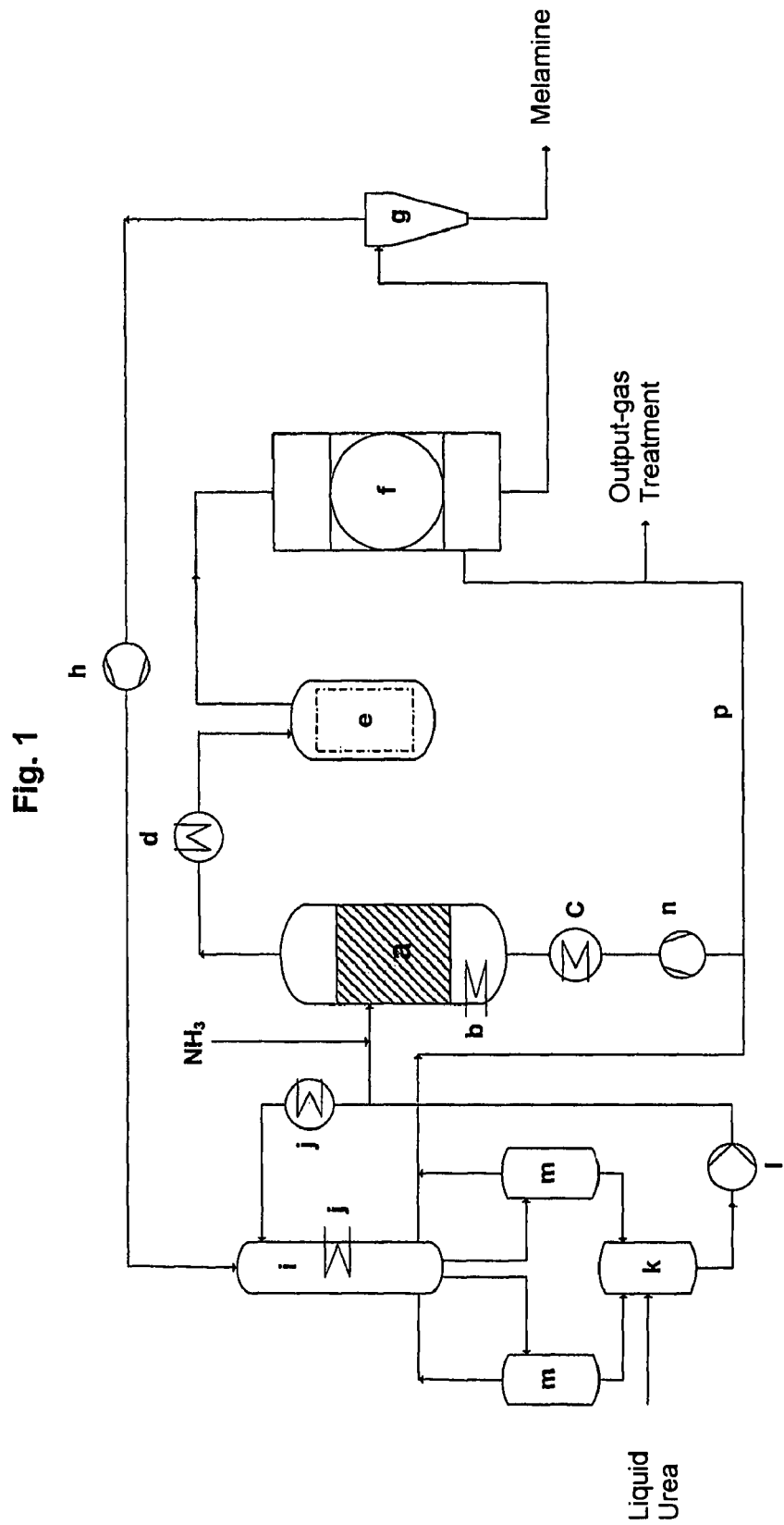
FIG. 1 is a schematic diagram showing a method of producing melamine according to the BASF process.

FIG. 1 shows the method of producing melamine according to the BASF process. Molten urea is fed to the system by means of a urea reservoir k. A pump l is used to feed urea to the urea washing station i; the liquid and gaseous components are separated from each other in a downstream mist collector m. A portion of the resulting gaseous components is compressed by a compressor n, preheated in a heating element c and then fed to the reactor a, where the components are required to form the catalytically acting fluidized bed. The gaseous components exiting the reactor a are cooled by a gas cooler d and then fed to a gas filter e. Precipitated by-products, such as melem, melam and catalyst discharge, are separated from the reaction gas in this gas filter e. The resulting reaction gas is then supplied to a crystallization device f where the gas is cooled with other reaction gases (quenching gas) that preferably have a temperature of approximately 140° C. to a temperature ranging between 190 and 200° C. The crystalline melamine obtained in the crystallization device is then supplied to a product cyclone g where the gaseous phase is separated from crystalline melamine. After separating the melamine, the gas is pumped to the urea washing station i by means of a recycle gas blower h.

Figure 2:
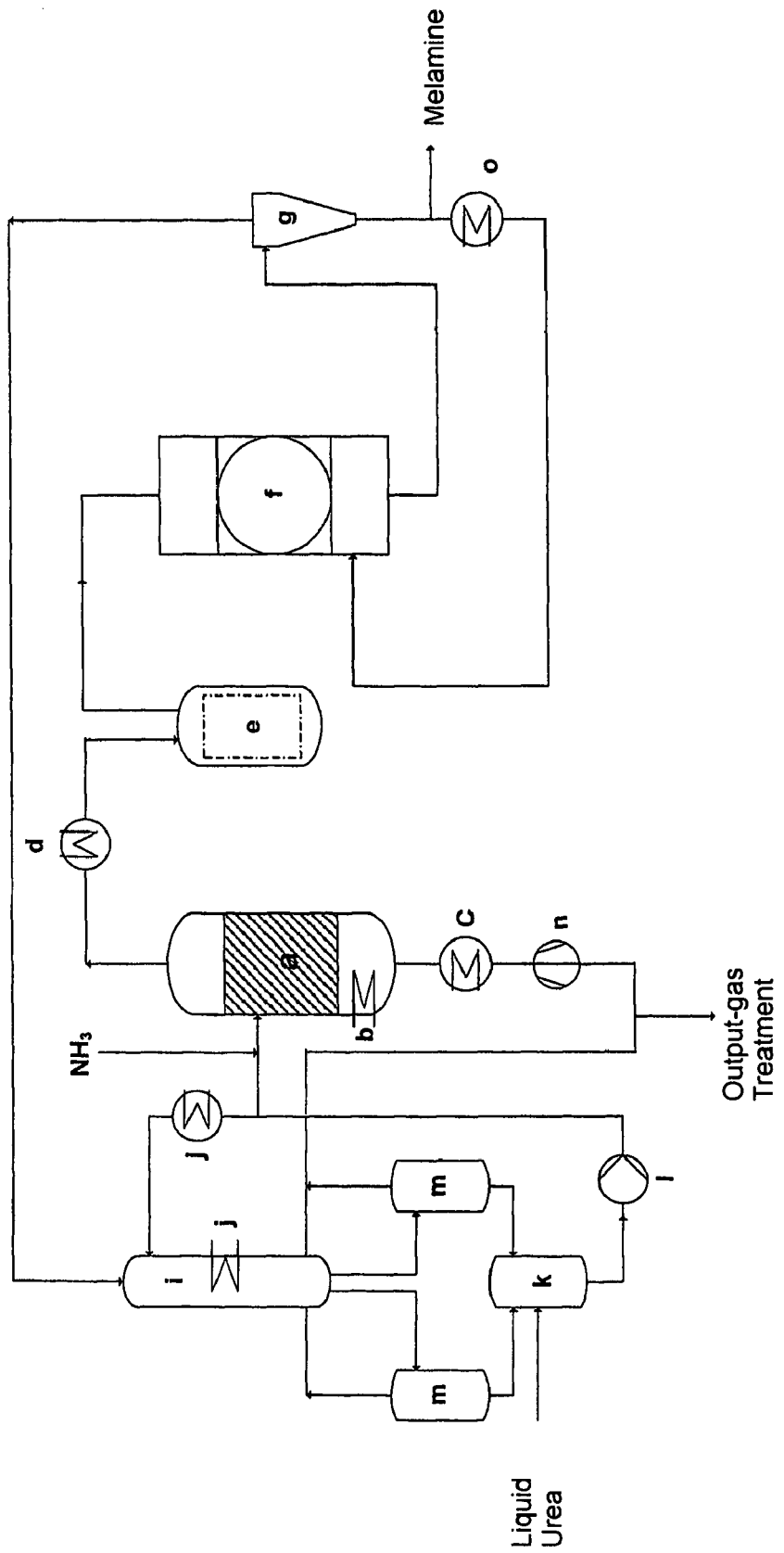
FIG. 2 is a schematic diagram showing the method according to the invention for producing melamine by introducing crystalline melamine.

FIG. 2 shows an inventive method of producing melamine by introducing crystalline melamine. Liquid urea is fed to the system by means of a urea reservoir k. Liquid urea is supplied to the urea-washing station i by means of a pump l and cooling unit j, subsequently liquid and gaseous components being separated from each other in a mist collector m. The gaseous components are compressed by a compressor n and heated in a gas heater c; the hot gases are then fed to the reactor a where they are required for making the catalytically acting fluidized bed. The gaseous components formed in the reactor are cooled in a gas cooler d and then fed to a gas filter e where crystallized components such as melem, melam and catalyst discharge are separated from the gaseous components. After this, the gaseous components are supplied to a crystallization device f, the gaseous components being cooled by crystalline melamine. The formed melamine is then separated from the gaseous components by a product cyclone g. A portion of the resulting melamine is cooled to a temperature of approximately 40° C. in a solid matter cooling unit o and is then reintroduced into the crystallization apparatus in order to cool the hot melamine-containing gas coming from the reactor. The gas that has been freed from melamine flows from the product cyclone g to the urea washing station i without any additional pumping devices. The quenching gas line p and the recycle gas blower h used in the BASF process are eliminated.

Figure 3:
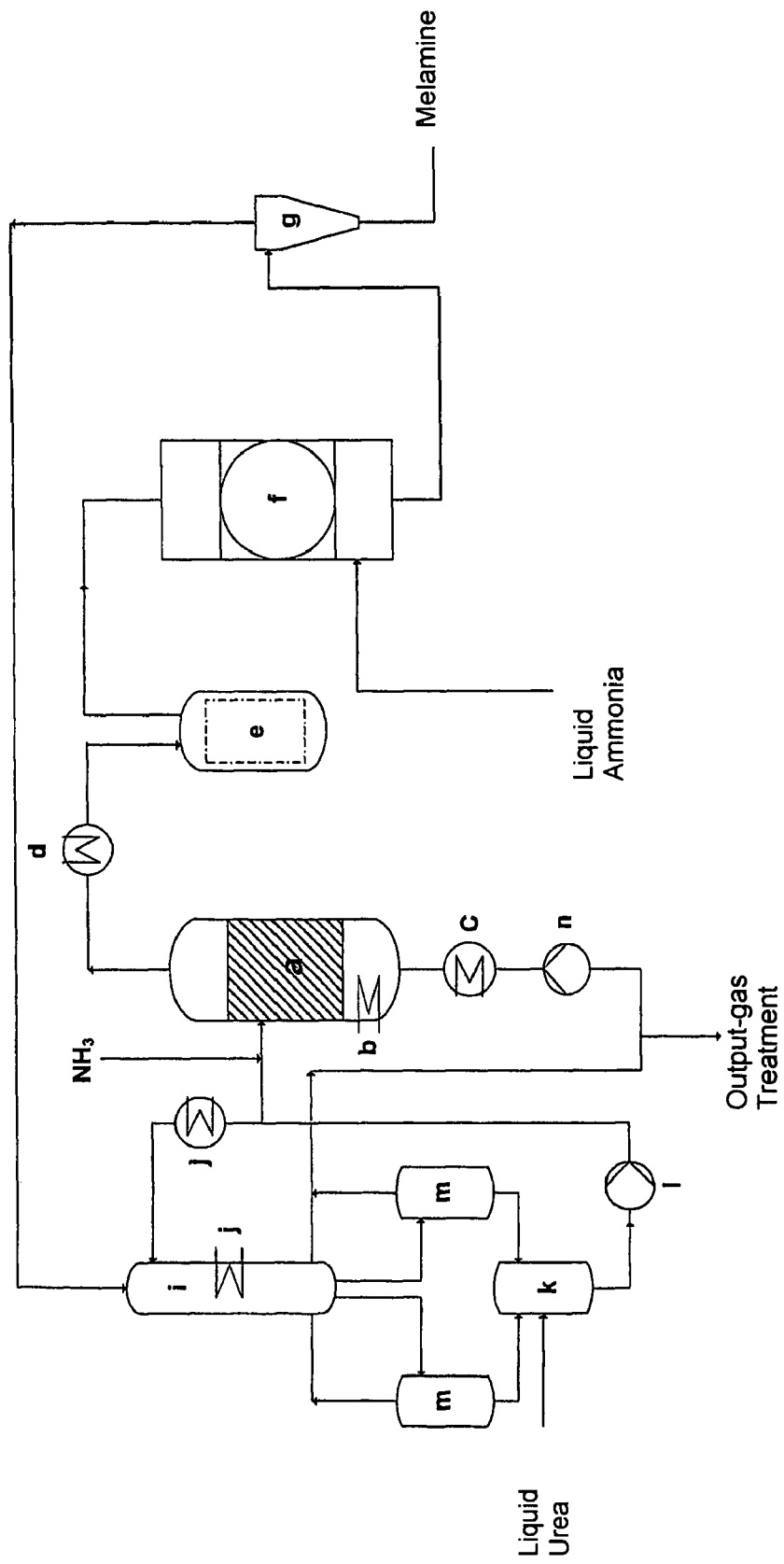
FIG. 3 is a schematic diagram showing the method according to the invention for producing melamine by introducing liquid ammonia.

FIG. 3 shows an inventive method of producing melamine by addition of liquid ammonia. Liquid urea is fed to the system from a urea reservoir k. Liquid urea is supplied to the urea washing station i by means of a pump l and cooling unit j, and subsequently liquid and gaseous components are separated from each other in a mist collector m. The gaseous components are compressed in a compressor n in the quantities required for the reaction, heated in a heater c and then fed to the reactor a. The gaseous components formed in the reactor are cooled in a gas cooler d and then fed to a gas filter e where crystallized components such as melem, melam and catalyst discharge are separated from the gaseous components. After this, the gaseous components are supplied to a crystallization device f, the gaseous components being cooled by liquid, evaporating ammonia. The formed melamine is then separated from the gaseous components by a product cyclone g. The gases that have been largely freed from solid melamine matter flow back to the urea washing station i.

The quenching gas line p and the recycle gas blower h used in the BASF process are also eliminated with this method.

The invention will be explained in more detail with the examples 1, 2 and 3.

EXAMPLE 1

Example 1 describes the familiar BASF process. After an intermediate cooling and filtration, the hot melamine-containing gas stream exiting the reactor has the following composition at a temperature of 320° C.

|  | kmol/h | mole % |
|---|---|---|
| Ammonia $NH_3$ | 1,709 | 67 |
| Carbon Dioxide $CO_2$ | 740 | 29 |
| Melamine $C_3H_6N_6$ | 51 | 2 |
| Isocyanic Acid HNCO | 38 | 1.5 |
| Inert | 31 | 0.5 |
| Total | 2551 | 100 |

The resulting melamine-containing gases are then contacted with the quenching gas in the crystallization device. The quenching gas, which typically comprises 30 mole % $CO_2$ and 70 mole % $NH_3$ and has a temperature of 138° C., lowers the temperature at the outlet of the crystallization device down to 205° C. Taking the desublimation enthalpy of melamine and the specific thermal capacity of the gas mixture into consideration, 7650 kmol/h of quenching gas is required. This corresponds to a ratio of approximately three parts of quenching gas to one part melamine-containing gas. The gas volume after the crystallization device and after separating the crystalline melamine is 10,200 kmol/h. The quantity of vaporous melamine that cannot be crystallized at a temperature of 205° C., is approximately 0.6 kmol/h.

EXAMPLE 2

Example 2 describes the inventive method of the desublimation of melamine by quenching with melamine crystals.

The hot melamine-containing gas in the same composition and same temperature as in Example 1 is supplied to the crystallization device with cooled melamine. The temperature of the cooled melamine is 40° C. Taking the desublimation enthalpy of melamine, the specific thermal capacity of the gas mixture as well as the specific thermal capacity of the solid melamine into consideration, 380 kmol/h of melamine is required for a mixture temperature of 230° C. after the crystallization device. After separating out the crystalline melamine, the amount of gas remaining is only 2500 kmo l/h. When comparing the circulating gas volume from this example with the gas volume from Example 1, the difference between them is a factor of four. Consequently, the apparatuses f, g, i and m (FIGS. 1 to 3) and the connecting pipes can be dimension ed half as large. The recycle gas blower h (FIG. 1) can be completely eliminated.

EXAMPLE 3

Example 3 describes the inventive method of the desublimation of melamine by liquid ammonia. After an intermediate cooling and filtration, the melamine-containing gas stream exiting the reactor a has the following composition at a temperature of 320° C.

|  | kmol/h | mole % |
| --- | --- | --- |
| Ammonia $NH_3$ | 2066 | 81 |
| Carbon Dioxide $CO_2$ | 383 | 15 |
| Melamine $C_3H_6N_6$ | 51 | 2 |
| Isocyanic Acid HNCO | 38 | 1.5 |
| Inert | 13 | 0.5 |
| Total | 2551 | 100 |

The hot melamine-containing gas is contacted with evaporated ammonia in the crystallization device. The temperature of the ammonia is 40° C. and the pressure is 0.16 MPa. If the same quantity of vaporous melamine as in Examples 1 and 2 is expected at the outlet of the crystallization device, 650 kmol/h of ammonia is required. The temperature at the outlet is 225° C. The amount of gas flowing to the urea-washing station after separating the crystalline melamine is 3,200 kmol/h. When comparing the circulating gas volume from this example with Example 1, a reduction of the gas volume by a factor of 3 is apparent. Compared to Example 1, consequently the dimensions of the following apparatuses are clearly reduced by a factor of 1.7: The urea-washing station, mist collector, crystallization device and product cyclone. The recycle gas blower (FIG. 1) can be completely eliminated.

LIST OF REFERENCE NUMERALS a) Fluidized bed reactor
b) Heating element
c) Gas heating element
d) Gas cooler
e) Gas filter
f) Crystallization device
g) Product cyclone
h) Recycle gas blower
i) Urea washing station
j) Cooling unit
k) Urea reservoir
l) Pump
m) Mist collector
n) Compressor
o) Solid matter cooler
p) Quenching gas line

The invention claimed is:
1. A method of producing crystal-line melamine in a single stage reaction, which comprises the steps of:
    (a) catalytically decomposing urea in a fluidized bed at a pressure of 0.1 to 1 MPa at a temperature of at least 380 to 410° C. using a carrier gas comprising ammonia or a mixture of ammonia and carbon dioxide to obtain a hot melamine-containing reaction gas;
    (b) providing a crystallization vessel, passing the hot melamine-containing reaction gas into the crystallization vessel, and simultaneously introducing crystalline melamine cooled to a temperature of less than 100° C. to approximately 40° C. into the crystallization vessel as a sole quenching means to cool and quench the hot melamine-containing reaction gas from approximately 350° C. to approximately 190° C. to desublimate the melamine in the hot melamine-containing reaction gas to obtain a crystalline melamine product, removing the hot melamine-containing reaction gas containing the crystalline melamine product from the crystallization vessel and separating the crystalline melamine product from said gas;
    (c) regulating the temperature of the crystalline melamine product removed from the crystallization vessel by the amount of the cooled crystalline melamine used for quenching the hot melamine-containing reaction gas, to reach a predefined target value that is not lower than 190° C.; and
    (d) following step (c), cooling in a solid matter cooler located outside the crystallization vessel at least a portion of the crystalline melamine product separated from said gas to a temperature of less than 100° C. to approximately 40° C. to obtain cooled crystalline melamine, and reintroducing the cooled crystalline melamine from the solid matter cooler into the crystallization vessel in step (b) so that the reintroduced cooled crystalline melamine is the sole quenching means according to step (b) to quench the hot melamine-containing reaction gas.
2. The method of producing crystalline melamine defined in claim 1 wherein according to step (d), the temperature of the crystalline melamine reintroduced into the crystallization vessel as cooled crystalline melamine to desublimate the melamine in the melamine-containing reaction gas is approximately 40° C.

* * * * *